United States Patent [19]

Vogel

[11] Patent Number: 5,876,118
[45] Date of Patent: Mar. 2, 1999

[54] CALORIMETER HAVING RAPID COOLING OF A HEATING VESSEL THEREIN

[75] Inventor: Herman Vogel, Newtown, Conn.

[73] Assignee: The Perkin-Elmer Corporation, Norwalk, Conn.

[21] Appl. No.: 569,368

[22] Filed: Dec. 8, 1995

[51] Int. Cl.[6] .......................... G01N 25/00; G01K 17/00
[52] U.S. Cl. .............................. 374/11; 374/33
[58] Field of Search .................................. 374/31, 33, 34, 374/36, 37, 10, 11, 13, 12

[56] References Cited

U.S. PATENT DOCUMENTS

| | | | |
|---|---|---|---|
| 3,263,484 | 8/1966 | Watson et al. | 73/15 |
| 4,653,732 | 3/1987 | Wunning et al. | |
| 4,809,190 | 2/1989 | Homer et al. | 374/36 |
| 5,098,196 | 3/1992 | O'Neill | 374/11 |
| 5,267,257 | 11/1993 | Jhawar et al. | |

FOREIGN PATENT DOCUMENTS

| | | |
|---|---|---|
| 0535319 | 4/1993 | European Pat. Off. |
| 62-188718 | 8/1987 | Japan |
| 5346413 | 12/1993 | Japan |
| 6216056 | 8/1994 | Japan |
| 7294465 | 11/1995 | Japan |
| 8157942 | 6/1996 | Japan |

OTHER PUBLICATIONS

"Heat Transfer by a Square Array of Round Air Jets Impinging perpendicular to a Flat Surface Including the Effect of Spent Air" by D.M. Kercher and W.Tabakoff, Gas Turbine Conference and Products Show, Cleveland OH, Paper No. 69–GT–4 (Mar. 9–13, 1969).

*Primary Examiner*—Richard Chilcot
*Assistant Examiner*—William L. Oen
*Attorney, Agent, or Firm*—Herbert S. Ingham; Edwin T. Grimes; David Aker

[57] ABSTRACT

A calorimeter apparatus includes a facility for rapid cooling of a heating vessel therein. A jacket surrounds the vessel wall. A partition member between the jacket and the vessel wall defines an inlet plenum adjacent the jacket and a spatial gap adjacent the vessel wall. Pressurized cooling gas is conveyed into the inlet plenum after termination of heating the vessel. The partition member has a distributed plurality of orifices such that the gas is jetted through the orifices to impingement cool the vessel wall. The gas is discharged from the spatial gap through an outlet plenum at an end wall of the vessel. The plurality of orifices are distributed in a pattern of varying density across the partition member such that uniform cooling of the vessel wall by the jetted gas is effected.

20 Claims, 2 Drawing Sheets

5,876,118

CALORIMETER HAVING RAPID COOLING OF A HEATING VESSEL THEREIN

This invention relates to calorimeters and particularly to the cooling of a heating vessel in a calorimeter.

BACKGROUND

A calorimeter is commonly used for providing measurements on thermal characteristics of samples. One such calorimeter is a differential scanning calorimeter (DSC) for making measurements on a pair of samples such that a test sample is compared to another test sample or a reference sample, for example, as described in U.S. Pat. No. 3,263,484 (Watson et al). The samples are supported in an insulated container. A power supply provides power to each of the samples and temperatures are measured. In a DSC, differential power and temperature between samples are determined for comparison of heating characteristics such as phase changes. A furnace or other heating vessel is placed over the sample region for heating to provide a range of temperatures for the measurements. Liquid nitrogen or the like in a reservoir below the sample support may be used to extend the DSC to a lower temperature range.

After a test run with a calorimeter to an elevated temperature, but before making another test run, it usually is necessary to cool the sample region back to a starting level which may be room temperature or liquid nitrogen temperature. Typically a cooling chamber surrounds the furnace, for cooling gas to be passed through the region between the chamber walls and the furnace. Such an arrangement is relatively slow to cool the furnace walls and the sample region within, because the air flowing over the walls is warmed and is thereafter inefficient in cooling other wall regions. Such a method generally takes at least 30 minutes to cool from 500° C. to room temperature. Furthermore, because of the non-uniform temperature of the resultant cooling air, the furnace walls vary in temperature, significantly affecting the performance of the calorimeter which then requires some corrective calculations to overcome the physical handicap.

High velocity jets have been used for cooling of surfaces, as disclosed in a paper "Heat Transfer by a Square Array of Round Air Jets Impinging perpendicular to a Flat Surface Including the Effect of Spent Air" by D. M. Kercher and W. Tabakoff, Gas Turbine Conference and Products Show, Cleveland Ohio, Paper No. 69-GT-4 (Mar. 9–13, 1969).

SUMMARY

An object of the invention is to provide an improved calorimeter with facility for rapid cooling of a heating vessel for test samples.

This and other objects are achieved, at least in part, by a calorimeter apparatus having a particular arrangement for cooling of a heating vessel therein. The apparatus comprises means for supporting a sample, and a heating vessel formed of a vessel wall encompassing the sample means for heating the sample therein. A jacket spaced from the vessel wall surrounds the heating vessel. A partition member, having a plurality of orifices therethrough, is affixed between the jacket and the vessel wall to define an inlet plenum between the partition member and the jacket, and further define a spatial gap between the partition member and the vessel wall. A heating means heats the vessel for a selected heating period. A gas means conveys a pressurized cooling gas into the inlet plenum after termination of the heating period. A discharge means discharges the cooling gas from the spatial gap. The plurality of orifices are distributed across the partition member such that the pressurized cooling gas is jetted through the orifices across the spatial gap to impinge on the vessel wall, whereby the vessel is rapidly cooled by the cooling gas.

Preferably the orifices are distributed in a pattern of varying density across the partition member such that uniform cooling of the vessel wall by the jetted gas is effected. In one such embodiment, the pattern has a first density at one end of the vessel, and a second density at the other end of the vessel, the second density being greater than the first density.

In another aspect, upon the termination of the heating period, the heating means inherently effects a local temperature at a local area of the vessel wall different than the average temperature of the vessel. For this aspect, the pattern of orifices has an average density in the general vicinity of the local area and a specific density at the local area. The specific density is greater than the average density for a local temperature greater than the average temperature, or less than the average density for a local temperature less than the average temperature.

DETAILED DESCRIPTION

Figure 1:
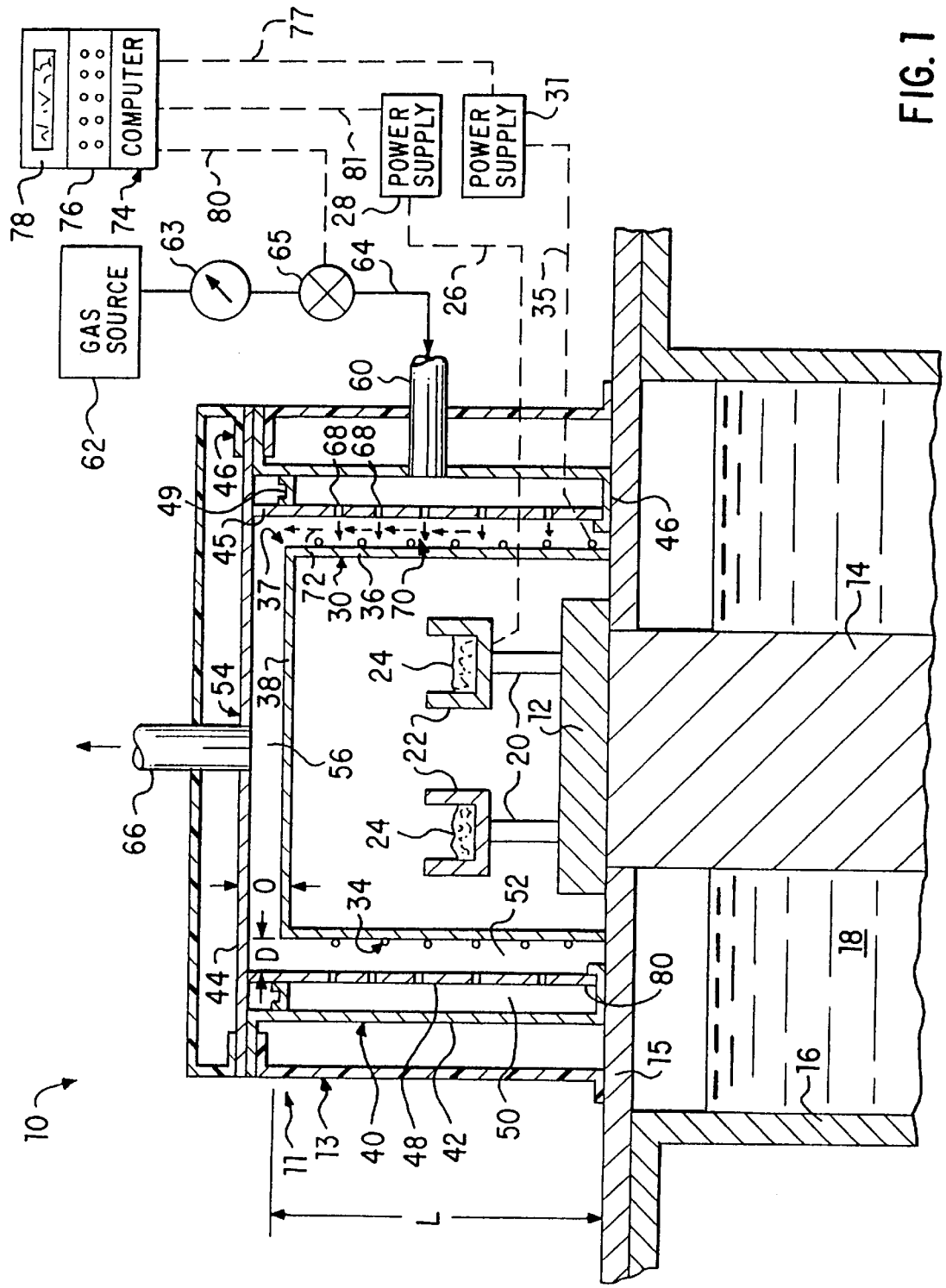
FIG. 1 is a partial vertical section of a calorimeter apparatus of the invention, with associated components shown schematically.

A calorimeter 10 such as a Perkin-Elmer model DSC-7 is used to incorporate the present invention. This model is a differential scanning calorimeter (DSC), but a simpler calorimeter may be used. Components are generally under an insulating cover 11 with an outer shell 13. The DSC has a metal base 12 resting on a deck 15 with a cooling block 14 extending down into a container 16 of liquid nitrogen 18, or other cooling medium, which is thereby in thermal communication with the sample. Supports 20 on the base hold a pair cups 22, each of which holds a sample 24. Via appropriate leads 26, a power supply 28 provides power to heating elements (not shown) in each of the sample cups, and temperatures are also measured. In a DSC, differential power and differential temperature between samples are determined for comparison of heating characteristics. A wide range of temperatures for the samples is provided by the liquid nitrogen through the base at one temperature extreme, and a heating vessel 30 placed over the sample region for heating to the other extreme, for example to 800° C. furnace temperature. The vessel heater has a separate, regulated power supply that incorporates temperature feedback. Thus the calorimeter is operational to range the sample temperature from a furnace temperature substantially higher than room temperature (generally about 20° C.) to a cryogenic temperature substantially lower than room temperature.

The heating vessel 30 is generally a conventional furnace, oven or other desired heating container with an accessible, external wall. The vessel is heated conventionally such as by an electrically resistive heating coil 34 wound on the outside of the cylindrical wall 36 of the vessel, with electrical current leads 35 from a regulated power supply 31 to the heating coil. Alternative heating means may be used, for example combustion in the vessel, or hot fluid passed between walls of a double walled oven. At one end 37 of the vessel is an end wall 38 attached to the main cylindrical wall 36 to close the vessel off at that end. The vessel should be metallic for thermal conductance, such as copper or stainless steel.

A jacket 40 surrounding the vessel 30 has a cylindrical portion 42 that encompasses the cylindrical wall 36 and is spaced therefrom. An end plate 44 is attached to the cylindrical portion to close off the end of the jacket at the closed end 37 of the furnace. Flanges 46 or other means may be provided for holding the components together and mounting to the rest of the calorimeter system.

A partition member 48 is affixed between the cylindrical portion 42 of the jacket and the furnace wall 36, for example with a bracket ring 49. An inlet plenum 50 is defined between the jacket and the partition, and a spatial gap 52 is defined between the furnace wall and the partition. A manifold 54 with an outlet plenum 56 therein is formed by the end wall 38, the end plate 44, and the adjacent cylindrical end 45 of the partition member. Although the furnace and associated components preferably are cylindrical for efficiency, as in the present example, other possible configurations include an oval or square cross section.

At least one inlet port 60 is provided centrally in one side of the cylindrical portion 42 of the jacket; one such port is shown but additional ports may be used to more evenly distribute the input of a cooling gas. The port (or ports) are receptive of a pressurized gas from a conventional source 62 such as an air compressor, a gas bottle with pressure regulator 63 or, preferably, a cryogenic gas such as from a container of liquid nitrogen. (As used herein and in the claims, the term "cryogenic gas" means gas obtained from the low temperature liquified phase of a substance that is gaseous at atmospheric temperature and pressure, such as liquid nitrogen, oxygen, hydrogen or helium.) A cryogenic gas is particularly useful for cooling of a calorimetric furnace because of its very low temperature (−196° C. boiling point), and more particularly advantageous where liquid nitrogen temperature is used in the calorimeter. Another gas such as helium may be selected for cooling ability. A further variation is to cool to about room temperature with compressed air or room temperature nitrogen, and switch to cryogenic nitrogen for further cooling.

In the case of cryogenic gas, pressure may be provided by heating the liquified gas, but advantageously is provided from an external compressed gas source such as dry nitrogen applied to the container of liquid nitrogen. The dry nitrogen should be introduced below the liquid level so as to bubble up to be cooled. Gas to the plenum is taken from over the liquid as a combination of the introduced and vaporized gases.

The gas is conveyed into the inlet plenum via a pipe 64, a regulator 63, an electrically operated (e.g. solenoid) on-off valve 65 and the port 60. Gas from the gap 52 is discharged by way of the outlet manifold 54 and its plenum 56 through an exit port 66 to ambient atmosphere or other lower pressure zone (relative to inlet pressure) or to a collection system for recovery or recycling.

The partition 48 has a plurality of orifices 68 therethrough. The orifices are of such a size in relation to the pressure drop across the partition as to pass the gas through the orifices in the form of jets 70 of the gas, advantageously nearly choked flow from a pressure in the plenum up to about one atmosphere above ambient pressure. The gap 52 is small enough in depth D for the jets to impinge on the vessel wall 36 so as to thereby cool it. However, the gap also is large enough in relation to volume of flow and the density pattern of the orifices 68 in the partition 48, so that spent gas 72 from the jets can flow towards the outlet plenum 56 without significantly interfering with the cooling action of the jets. A suitable dimension for the gap D may readily be determined empirically, by measurement of the cooling effects. The partition member should be as thin as practical to minimize energy loss for the jets, for example 0.2 mm.

A computer 74 is generally associated with a modern DSC or other calorimeter to control the heating via the power supplies 28, 31 and respective cables 81, 77. The computer receives measurement signals of power and temperature back through the cables, and effects computations of the desired thermal characteristics of the sample. The computer may be conventional such as a Digital Corporation (DEC) model 433dxMT incorporated into the DSC by the manufacturer thereof. The computer should include a central processing unit (CPU) with appropriate analog/digital converters (in and/or out as required), memory sections including disk drive RAM and/or firmware, a keyboard or keypad 76 for operator input, and an information display 78 and/or a printer. Programming is conventional such as with "C" generally incorporated into the computer by the manufacturer of the computer or the instrument. In the present case the computer preferably also controls the gas valve 65 via line 80 upon termination of vessel heating via the power supply control line 81. Adaptations of the programming for the present invention will readily be recognized and achieved by those skilled in the art.

In operation the furnace is heated for a selected heating period of time for the ordinary or other desired measurements with the calorimeter. After the heating is terminated, and preferably immediately thereafter, the gas flow is initiated to rapidly cool the furnace back down to a desired temperature. The termination of heating and opening of the valve 65 may be controlled by the computer. Ordinarily measurements are taken during the heating, but alternatively, or in addition, they may be taken during cooling.

Figure 2:
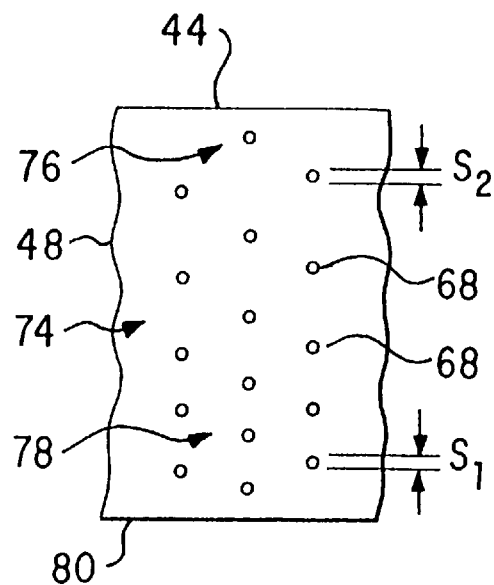
FIG. 2 is an elevation of a portion of a partition member of the apparatus of FIG. 1, showing one embodiment of a pattern of orifices therein.

According to a preferred embodiment, the orifices 68 are distributed in a pattern of varying density across the partition member such that uniform cooling of the vessel wall by the jetted gas is effected. ("Density" means number of orifices per unit area.) In one embodiment (FIG. 2) the pattern 74 compensates for the additional cross flow that occurs from the spent gas 72 (FIG. 1) flowing to the outlet plenum. In this case, the pattern has a first density in the region 76 proximate the outlet end 44 and a second density in the region 78 proximate the other end 80 of the gap opposite from the manifold. The second density is greater than the first density so as to effect a higher density of jets impinging at the inner end 80, a lower density at the other end, and a gradation from higher to lower between the ends. The jets are further apart toward the manifold end to accommodate the outgoing flow 72 and smooth out the cooling. It has been determined that, for a furnace having an aspect ratio of about one, the second density should be at least 50% greater than the first density, for example about 100% greater (i.e. twice the density). Aspect ratio is defined conventionally as the ratio of the length L of the furnace vessel parallel to the direction of gas outflow to the average orthogonal dimension D, typically diameter. More generally, the second density should be greater than the first density by a factor of about 25% to 75%, for example 50%, of the aspect ratio L/D.

Figure 3:
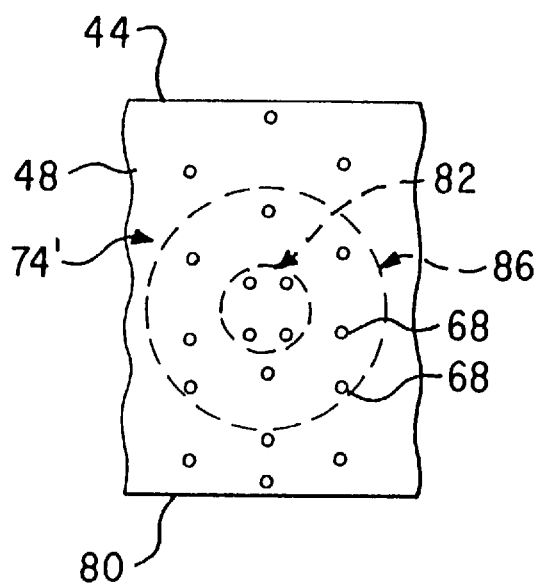
FIG. 3 is an elevation of a portion of a partition member of the apparatus of FIG. 1, showing another embodiment of a pattern of orifices therein.

In another embodiment (FIG. 3) of the varying density, a different pattern 74' of orifices is established to compensate for hot or cool spots on the furnace wall. The heating means generally effects an average temperature of the vessel wall. Additionally, by an irregularity in the coil or an internal proximity or the like, the heating means inherently may effect a local temperature at a local area 82 of the vessel wall different than the average temperature. The orifice pattern will have an average density in the general vicinity 86 of the local temperature area 82. Such average density may be the overall density if such is uniform. Preferably the density also will vary from one end to the other as explained above (and included in FIG. 3), in which case the average density in the general vicinity is that of the pattern near the temperature spot but outside the immediately adjacent area. Then there should be a another specific density at the local area 82, the specific density being greater than the average density for a local temperature greater than the average temperature or less than the average density for a local temperature less than the average temperature. No precise example will have much significance as it would depend on the exact nature of the hot or cool spot. However, for example, the specific density may be double that of the average where a hot spot temperature at the start of the cooling is 10° C. above the average.

In a further embodiment (FIG. 2), it is desirable to vary the orifice sizes (diameters) $S_1$, $S_2$ inversely to the orifice density, preferably approximately in inverse proportion. The purpose is to keep local flow rates at a minimum while performing optimal local cooling. Broadly, the orifice size preferably is varied by a factor that is between about half and double the inverse proportion.

The variations in density and size of orifices may be determined experimentally. Alternatively and advantageously, the densities and sizes are calculated, for example in accordance with the principles set forth in the aforementioned paper by Kercher et al. (incorporated herein by reference) taking into account differences in temperature, pressure, and cool down rather than steady state.

For example, a furnace vessel is 4 cm long and 4 cm diameter, thereby having an aspect ratio of one. A suitable orifice spacing for this is 5 mm at the inner end and 15 mm at the discharge end, having respective densities of 4 orifices/cm$^2$ and 1.3 orifices/cm$^2$; i.e. the outer density is about ⅓ the inner density (ratio of 1.3 to 4). A suitable corresponding orifice size $S_1$ is 0.5 mm at the inner end and the size $S_2$ is 1.5 mm at the discharge end, the inverse proportionality factor for the density thus being three.

In an example for orifice size, if the half of the inverse proportion is selected for the factor, the orifice size at the outer end will be 0.75 mm. If double the inverse proportion is selected, the orifice size at the outer end will be 3 mm.

Further dimensions, for the foregoing aspect ratio of one, are a width W of 4 mm for the inlet plenum, 4 mm for the spatial gap width, and 4 mm space O for the outlet plenum. With such an arrangement, and orifice sizes ranging from 5 mm to 15 mm as described above, a cryogenic nitrogen pressure of 70,000N/mm$^2$ gage (10 psig) is suitable for the cooling gas flow. Typically this can drop the temperature from 500° C. to room temperature in five minutes, and to −180° C. in another two minutes. For the same flow rates, the present impingement cooling techniques are up to six times faster than the conventional cooling technique for calorimeters where the gas merely flows over the surface. While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. A calorimeter apparatus with facility for rapid cooling of a heating vessel therein, the apparatus comprising means for supporting a sample, a heating vessel formed of a vessel wall encompassing the sample, means for heating the sample, a jacket surrounding the vessel spaced from the vessel wall, a partition member affixed between the jacket and the vessel wall to define an inlet plenum between the partition member and the jacket and a spatial gap between the partition member and the vessel wall, heating means for heating the vessel for a selected heating period, gas means for conveying a pressurized cooling gas into the inlet plenum after termination of the heating period, and discharge means for discharging the cooling gas from the spatial gap, wherein the partition member has a plurality of orifices therethrough that are distributed across the partition member such that the pressurized cooling gas is jetted through the orifices across the spatial gap to impinge on the vessel wall, whereby the vessel is rapidly cooled by the cooling gas.

2. The apparatus of claim 1 wherein the discharge means comprises an outlet manifold located proximate a first end of the vessel wall, the manifold being receptive of the cooling gas from the spatial gap and having an exit port for the cooling gas.

3. The apparatus of claim 1 wherein the orifices are distributed in a pattern of varying density across the partition member such that uniform cooling of the vessel wall by the jetted gas is effected.

4. The apparatus of claim 3 wherein the orifices have orifice sizes varying by a factor in inverse proportion to the varying density of the pattern.

5. The apparatus of claim 3 wherein, upon the termination of the heating period, the heating means has effected an average temperature of the vessel wall, and has inherently effected a local temperature at a local area of the vessel wall different than the average temperature, and the pattern has an average density in the general vicinity of the local area and a specific density at the local area, the specific density being greater than the average density for a local temperature greater than the average temperature, or less than the average density for a local temperature less than the average temperature.

6. The apparatus of claim 5 wherein the orifices have an average size opening, and further have an opening size greater than the average size where the specific density is less, and an opening size less than average size where the specific density is greater.

7. The apparatus of claim 3 wherein the discharge means is located at a first end of the vessel wall, and the pattern has a first density at the first end and a second density at a second end of the vessel opposite from the first end, the second density being greater than the first density.

8. The apparatus of claim 7 wherein the vessel wall is generally cylindrical with an aspect ratio of length to diameter, and the second density is greater than the first density by a selected factor of about 25% to 75% of the aspect ratio.

9. The apparatus of claim 7 wherein the orifices have an average size opening, and further have an opening size greater than the average size where the specific density is greater, and an opening size less than average size where the specific density is less.

10. The apparatus of claim 7 wherein, upon the termination of the heating period, the heating means has effected an average temperature of the vessel wall, and has inherently effected a local temperature at a local area of the vessel wall different than the average temperature, and the pattern has an average density in the general vicinity of the local area and a specific density at the local area, the specific density being greater than the average density for a local temperature greater than the average temperature or less than the average density for a local temperature less than the average temperature.

11. The apparatus of claim 7 wherein the orifices have orifice sizes varying by a factor in inverse proportion to the varying density of the pattern.

12. The apparatus of claim 11 wherein the vessel has an end wall attached to the vessel wall at the first end, and the discharge means comprises an outlet manifold comprising the end wall and a further wall with an exit port therein for the cooling gas, the outlet manifold being receptive of the cooling gas from the spatial gap.

13. The apparatus of claim 12 wherein the vessel wall and the partition member are cylindrical, and the jacket comprises a cylindrical portion surrounding the partition member.

14. The apparatus of claim 13 wherein the gas means includes an inlet port for conveying the pressurized gas into the inlet plenum.

15. The apparatus of claim 14 wherein the vessel wall has an aspect ratio of length to diameter, and the second density is greater than the first density by a selected factor of about 25% to 75% of the aspect ratio.

16. The apparatus of claim 15 wherein, upon the termination of the heating period, the heating means has effected an average temperature of the vessel wall, and has inherently effected a local temperature at a local area of the vessel wall different than the average temperature, and the pattern has an average density in the general vicinity of the local area and a specific density at the local area, the specific density being greater than the average density for a local temperature greater than the average temperature or less than the average density for a local temperature less than the average temperature.

17. The apparatus of claim 16 wherein the factor is between about half and double of inverse proportion to the density.

18. The apparatus of claim 11 wherein the factor is between about half and double of inverse proportion to the density.

19. The apparatus of claim 1 wherein the cooling gas is a cryogenic gas.

20. The apparatus of claim 19 wherein the calorimeter includes a container for liquified gas such that the liquified gas is in thermal communication with the vessel, whereby the vessel, and thereby the sample, is rapidly cooled from furnace temperature to cryogenic temperature cooperatively by the cryogenic cooling gas and the liquified gas.

* * * * *